US008069738B2

(12) United States Patent
Lopez et al.

(10) Patent No.: US 8,069,738 B2
(45) Date of Patent: Dec. 6, 2011

(54) PROBE

(75) Inventors: Martin Lopez, Rotherfield (GB); James Hobby, Crowborough (GB); Richard P. Kovacich, Crowborough (GB)

(73) Assignee: Servomex Group Limited (GB)

( * ) Notice: Subject to any disclaimer, the term of this patent is extended or adjusted under 35 U.S.C. 154(b) by 852 days.

(21) Appl. No.: 11/971,955

(22) Filed: Jan. 10, 2008

(65) Prior Publication Data

US 2008/0168851 A1 Jul. 17, 2008

(30) Foreign Application Priority Data

Jan. 12, 2007 (GB) .................................. 0700677.8

(51) Int. Cl.
*G01N 1/14* (2006.01)
(52) U.S. Cl. .................................................. 73/863.83
(58) Field of Classification Search .................. None
See application file for complete search history.

(56) References Cited

U.S. PATENT DOCUMENTS

| 1,967,428 | A | * | 7/1934 | Quereau ...................... 356/438 |
| 4,126,396 | A | * | 11/1978 | Hartmann et al. ............ 356/434 |
| 4,161,883 | A | | 7/1979 | Laird et al. |
| 4,279,142 | A | | 7/1981 | McIntyre |
| 4,549,080 | A | | 10/1985 | Baskins et al. |
| 4,578,986 | A | * | 4/1986 | Navarre ........................ 73/61.59 |
| 4,852,384 | A | * | 8/1989 | Woolbert et al. ............. 73/1.07 |
| 5,297,432 | A | * | 3/1994 | Traina et al. ............... 73/864.34 |
| 5,423,228 | A | | 6/1995 | Budd et al. |
| 5,507,192 | A | * | 4/1996 | Beaudin ...................... 73/863.33 |
| 5,517,314 | A | * | 5/1996 | Wallin .......................... 356/437 |
| 5,781,306 | A | * | 7/1998 | Hartig et al. .................. 356/436 |
| 2003/0090666 | A1 | | 5/2003 | Kaufmann |
| 2003/0090667 | A1 | * | 5/2003 | Kaufmann .................... 356/438 |
| 2003/0110950 | A1 | | 6/2003 | Sjostrom et al. |

FOREIGN PATENT DOCUMENTS

| CN | 1414373 A | 4/2003 |
| GB | 1170047 A | 11/1969 |

OTHER PUBLICATIONS

Communication from the European Patent Office including European Search Report for EP Application No. 08250128, dated May 26, 2008, 8 pages.
Letter dated May 28, 2010 to the European Patent Office for EP Application No. 08250128 in reply to Examination Report dated Jan. 20, 2010, 5 pages.
Communication and Examination Report dated Jan. 20, 2010 from the European Patent Office for EP Application No. 08250128, 6 pages.
Letter dated Aug. 24, 2009 to the European Patent Office for EP Application No. 08250128 in reply to Examination Report dated Feb. 13, 2009, 4 pages.
Communication dated Feb. 13, 2009 from the European Patent Office for EP Application No. 08250128, 1 page.

(Continued)

*Primary Examiner* — Robert Raevis
(74) *Attorney, Agent, or Firm* — Daly, Crowley, Mofford & Durkee, LLP

(57) ABSTRACT

The present invention relates to a probe having an elongated main body with a proximal end for attachment to a wall of a duct or volume and a distal end that is disposed on the interior of the duct, such that the main body forms a measurement space through which the fluid is drawn for analysis.

12 Claims, 2 Drawing Sheets

OTHER PUBLICATIONS

Communication and Extended European Search Report dated May 26, 2008 from the European Patent Office for EP Application No. 08250128, 8 pages.

Office Action dated Jun. 3, 2010 from the State Intellectual Property Office of People's Republic of China for Chinese Appl. No. 200810002655.7, 3 pages.

Summons to attend Oral Proceedings pursuant to Rule 115(1) EPC, dated Feb. 23, 2011 in European Application No. 08250128.9, 9 pages.

Written submission dated Apr. 6, 2011 in reply to the summons to attend Oral Proceedings in European Application No. 08250128.9, 23 pages.

Second Office Action dated Dec. 23, 2010 in Chinese Application No. 200810002655.7, 10 pages.

Comments for Response to Office Action dated May 3, 2011 in Chinese Application No. 200810002655.7, 2 pages.

Response to the first examination report in corresponding Chinese Application No. 200810002655.7 filed in the Chinese Patent Office on Oct. 18, 2010, 5 pages.

* cited by examiner

PROBE

CROSS REFERENCE TO RELATED APPLICATIONS

This application claims priority under 35 U.S.C. §119 to Great Britain patent application No. GB0700677.8 filed on Jan. 12, 2007, which is incorporated herein by reference.

The present invention relates to a probe for use in analysis of sample fluid streams.

For many years optical methods such as absorption and luminescence measurements have been used for constituent gas analysis of sample streams. A common technique is open path cross stack gas absorption monitoring. This typically involves sending an optical beam from a source at one side of gas stack or duct to a detector at the other side and measuring the amount of optical absorption of the beam due to the target gas within the sample gas stream from which the gas concentration may be inferred. It may involve multiple passes in order to increase the absorption path length and hence enhance the detection limit.

However, in order to function effectively, the optical path from source to detector must be accurately aligned, this requires high precision and associated installation costs. Additionally, if there are particulates in the sample stream, they could obscure and/or damage the optical elements at the source and detector. This requires the optical elements to be continuously purged using a non-absorbing gas such as nitrogen or instrument air. This has associated costs and gas supply issues and also decreases the optical absorption path. Furthermore, if any change in purge gas flow rate or composition occurs, this could lead to measurement errors. Another problem associated with particulates in the gas stream is the fact that they will either absorb or scatter the light along the absorption path, leading to decreased resolution and possible errors. It is also difficult to accurately calibrate the device in situ.

The present invention provides a probe comprising an elongate main body having a proximal end for attachment to a wall of a duct and a distal end arranged to be disposed in the interior of the duct, the main body forming an optical cavity through which gas to be analysed is drawn.

The present invention therefore provides a probe whereby the sample gas is simultaneously sampled and analysed within a particulate free environment.

A preferred embodiment of probe allows in situ analysis e.g. of a target gas in a gas mixture within a chamber or volume via an optical absorption method by pulling a gas sample through a filter by aspiration or other means into an optical cavity housed within the probe where analysis occurs, the sample gas is then vented back into the sample stream or elsewhere. This means that the optical cavity is situated within the sample environment as opposed to being an extracted sample. A light beam from an optical source passes through an optical element into the probe, passes through the gas where absorption may occur, is reflected back from the end of the probe by a reflective element, passes back through the gas and out the probe onto a detector. The amount of attenuation of the input optical power is related to the concentration of the target gas. The analytical means may be by direct absorption measurements, gas filter correlation, tunable laser diode spectroscopy or other appropriate means. The drawing of the sample gas through the filter ensures a faster response than could be achieved by diffusion means and since analysis takes place in situ, it is also faster than an extractive means. The filtered environment within the optical cavity means that the input, output and reflective optical elements do not have to be maintained clear by using a purge gas arrangement. This probe also allows for the measurement or monitoring of the gas flow through the cavity by situating a flow sensor in line with the sample gas, which could, for example, indicate a blockage in the filter or a fault in the drawing means, and allows determination that an actual sample is being drawn into the measurement cavity, something which cannot be ascertained by using diffusion means. Any such blockage in the filter could be cleared by a reverse flow of a purge gas at high pressure through the cavity and vented through the filter. This ensures a fast, accurate measurement of the sample gas and an accurate in situ calibration can be maintained.

Accurate, in situ calibration can take place by means of a calibration port situated in the probe. A second flow sensor may also be installed to measure or monitor the flow rate of the calibration gases into the cavity. This enables more accurate control of the calibration to take place.

A switching valve arrangement could also be employed to allow the use of only one flow sensor to measure both the sample and calibration gas flow rates by selection of the appropriate flow path.

In order that the present invention be more readily understood, the embodiments will now be described by way of example with reference to the following figures.

Figure 1:
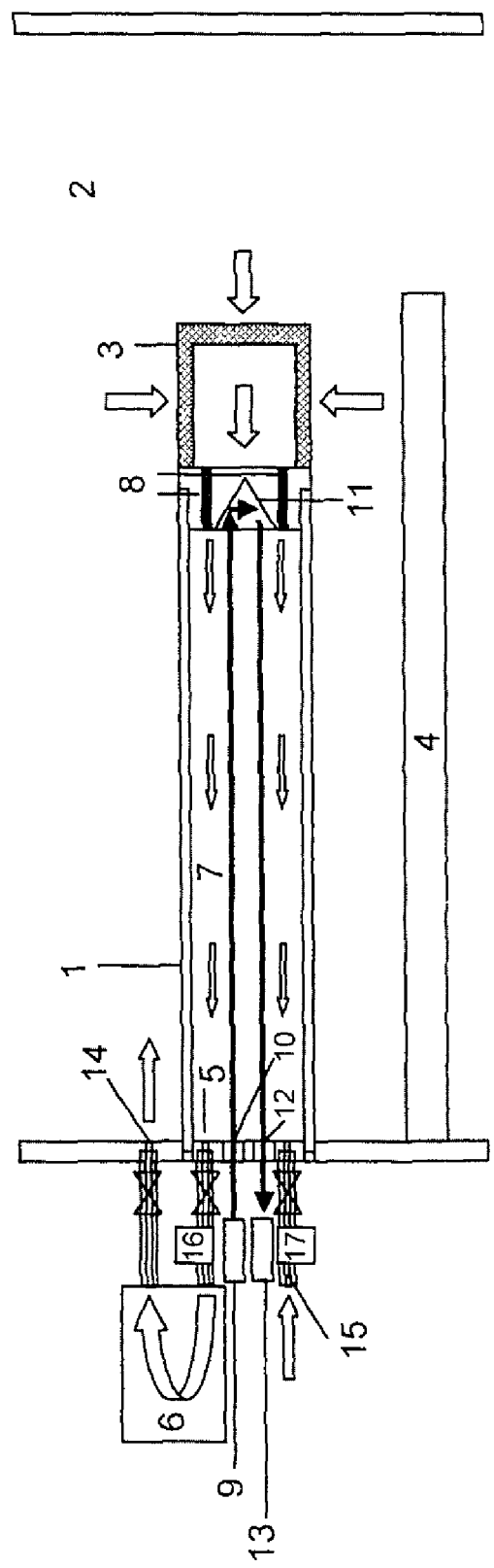
FIG. 1 shows a diagrammatic cross-sectional side view of a probe according to the present invention in situ in a duct.

According to the arrangement in shown in FIG. 1, a gas probe (1) is inserted into a gas duct (2) and a sample is drawn into the main of the probe body via a filter element (3). This filter element may be of sintered stainless steel, porous ceramic or similar appropriate material and design depending on the temperature and composition of the sample gas. A deflector shield (4) may also be used in the duct if appropriate to protect the probe in particularly abrasive environments. The sample is drawn through a sample drawing means (5) using such means as an aspirated system or a mechanical pump (6). This means may be housed within the main body of the probe or externally, possibly within a temperature controlled environment to prevent the formation of condensate which could lead to corrosion.

Once the gas sample has been drawn in through the filter, it is then drawn into an optical cavity (7) via a secondary filter or inlet apertures (8). A beam of light is passed from an optical source (9) into this optical cavity via an inlet optical element (10) and if any absorbing target gas is present, it will be attenuated by an amount related to the type of gas, its concentration, path length, background gases and ambient pressure and temperature. This light beam is then reflected back via a reflective optical element (11) to the outlet optical element (12) which may be identical to or different from the inlet optical element. The reflective optical element may be a corner cube, prism, planar mirror arrangement or other such suitable means. The optical pathway may involve multiple passes within the optical cavity in order to increase the absorption path length and hence enhance the resolution. Equally, the arrangement may involve multiple light beams of the same or different wavelength(s) within the optical cavity. This is achieved by appropriate design and materials of the optical cavity and optical and reflective elements. The reflected beam is then passed to a detector (13) where the optical power can be measured and hence the concentration of the target gas deduced. The sample gas within the probe housing is vented back to the sample gas stream or elsewhere via the vent means (14).

This gas probe incorporating the optical absorption measurement means has the advantages of reduced installation time, since the optical path is aligned at the factory and a defined absorption path length. It does not require continuous purge gas to clean the optical elements and is able to be accurately calibrated in situ by displacing the sample gas within the optical cavity with calibration gas via a calibration inlet (15) with the sample gas drawing means (5) closed via a valve. The calibration port may be incorporated into a modified sample gas drawing means. The calibration gas is vented back into the sample stream via the filter (3). The flow rate of the gas being drawn through the cavity may be measured or monitored via a flow sensor (16). If a reverse purge is required to unblock the filter, this can take place via the calibration port (15) or similar. A second flow sensor may be installed (17) to measure or monitor the flow rate of the calibration gases into the cavity. In the arrangement depicted in FIG. 1, this feature is illustrated with two separate flow sensors (16) and (17).

Figure 2:
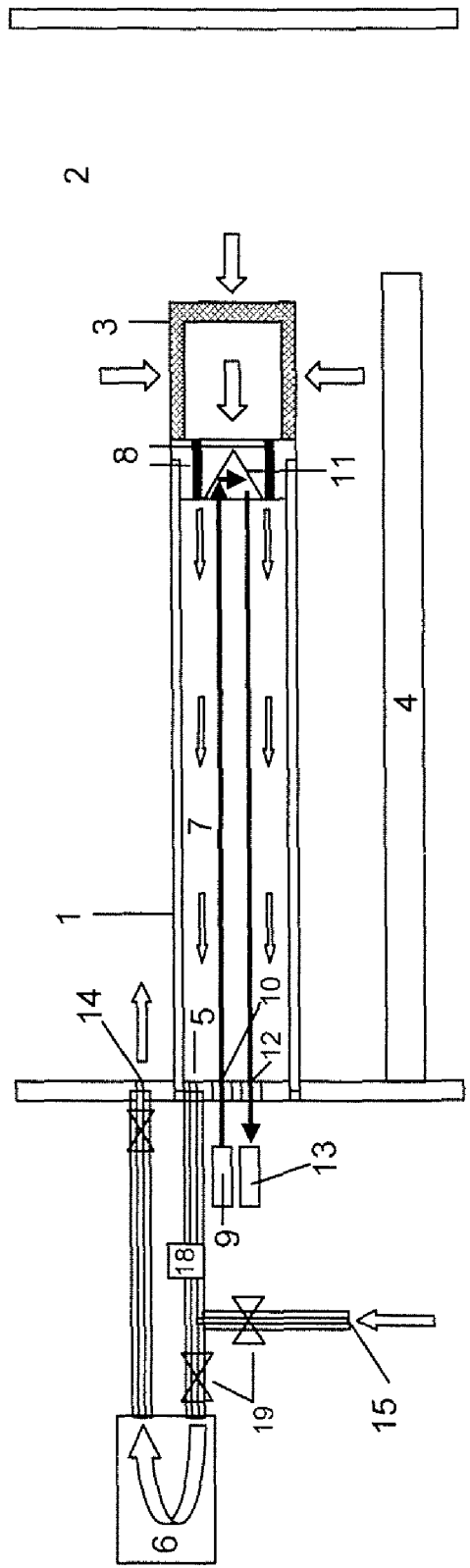
FIG. 2 shows a diagrammatic cross-sectional side view of an alternate arrangement of the probe according to the present invention.

In the alternate arrangement of the probe depicted by FIG. 2 the above two flow sensors are replaced by a single flow sensor (18) for measuring both the sample fluid flows and calibration fluid flows by use of a valve arrangement (19), which selects between the two different fluid flows. All other features of the probe in FIG. 2 are similar to the arrangement described above in FIG. 1, with the reference numerals referring to the same features as referred in FIG. 1.

Since the sample gas is drawn into the optical cavity and the analysis takes place simultaneously, the response time of the analytical means is much faster than could be achieved by a diffusion means or external sampling system and also allows determination that an actual sample is being drawn into the measurement cavity, The optical absorption method used to deduce the target gas concentration could be by using single or multiple wavelength direct absorption measurements, gas filter correlation spectroscopy, tunable laser diode spectroscopy or other appropriate technique(s). Optical emission techniques such as luminescence spectroscopy, whereby the target gas concentration is deduced by the luminescence intensity and/or decay times following excitation (optical or otherwise) of the target gas molecules may also employ the described means.

Although this method has been illustrated for an optical system as the preferred embodiment, this probe could equally well be used for other analytical methods such as acoustic or photoacoustic analysis, through appropriate modification of the optical cavity and elements. It could also be used for any fluid environment: gas, liquid or plasma or where the sample component of interest is carried within a fluid matrix.

The preferred embodiment has the probe provided on a flange which is also fitted with the necessary gas inlets and outlets so that only a single opening need be made in the duct carrying the gas to be analysed. The deflector, if provided, can also be fitted to the flange.

The invention claimed is:

1. A probe (1) for simultaneously sampling and analyzing fluids, comprising:
    an elongate main body having a proximal end for attachment to a wall of a duct (2) containing fluid to be analyzed, and a distal end arranged for positioning in the interior of the duct (2), the elongate main body forming a cavity (7) through which fluid to be analyzed can be drawn;
    an optical source (9) arranged to direct a beam of light into the cavity (7);
    an optical detector (13) arranged to detect the beam of light after passing through the cavity (7);
    a filter (3);
    means (5) for drawing the fluid to be analyzed into the cavity (7) through the filter (3);
    means for generating a reverse flow of fluid through the cavity (7), for venting the fluid through said filter (3); and
    a flow sensor (16) capable of monitoring a fluid flow rate of the fluid to be analyzed when being drawn into the cavity (7), to determine successful drawing of the fluid into the cavity (7).

2. A probe according to claim 1, further comprising means (15) to input calibration fluid into the probe.

3. A probe according to claim 2, comprising a further flow sensor (17) for monitoring a calibration fluid flow rate.

4. A probe according to claim 2 wherein said flow sensor is further capable of monitoring a calibration fluid flow rate and wherein a valve arrangement (19) is provided to allow monitoring of the fluid flow rate of a selected one of the fluid to be analyzed or the calibration fluid.

5. A probe according to claim 2, wherein the means for generating a reverse flow comprises means to input a reverse fluid flow via the means (15) to input calibration fluid.

6. A probe according to claim 1, comprising one or more flow sensors (16, 17, 18) arranged such that the sensors are in line with the fluid flow to be monitored.

7. A probe according to claim 1, wherein the filter (3) is provided in the distal end of the probe.

8. A probe according to claim 1, further comprising an optical element (10) via which the beam of light is able to enter the cavity (7).

9. A probe according to claim 8, further comprising a reflective element (11) arranged to reflect the beam of light one or more times within the cavity (7) to create an increased absorption path length.

10. A probe according to claim 9, where multiple beams of the same or different wavelengths are used for the measurement of the same of different target gases within the cavity.

11. A probe according to claim 8, further comprising an outlet optical element (12) for the light beam to exit the cavity (7) in the direction of the optical detectors (13) that is arranged to detect the light beam after the light beam passes through the outlet optical element (12).

12. A probe according to claim 1, where a deflector shield (4) is fitted to reduce abrasion due to particulates in a fluid stream.

* * * * *

UNITED STATES PATENT AND TRADEMARK OFFICE
CERTIFICATE OF CORRECTION

| | | |
|---|---|---|
| PATENT NO. | : 8,069,738 B2 | Page 1 of 1 |
| APPLICATION NO. | : 11/971955 | |
| DATED | : December 6, 2011 | |
| INVENTOR(S) | : Martin Lopez et al. | |

It is certified that error appears in the above-identified patent and that said Letters Patent is hereby corrected as shown below:

Column 1, After Line 3, insert --Field of the Invention--.

Column 1, After Line 5, insert --Background of the Invention--.

Column 1, Line 15-16, delete "of gas" and replace with --of a gas--.

Column 1, Line 46, delete "of probe" and replace with --of a probe--.

Column 1, Line 58, delete "out the" and replace with --out of the--.

Column 2, Line 32, delete "in shown" and replace with --as shown--.

Signed and Sealed this
Tenth Day of April, 2012

David J. Kappos
*Director of the United States Patent and Trademark Office*